(12) United States Patent
Green et al.

(10) Patent No.: US 7,745,118 B2
(45) Date of Patent: Jun. 29, 2010

(54) COMPARATIVE GENOMIC RESEQUENCING

(75) Inventors: Roland D Green, Madison, WI (US);
Steve Smith, Fitchburg, WI (US);
Thomas Albert, Fitchburg, WI (US);
Emile F. Nuwaysir, Madison, WI (US)

(73) Assignee: Roche Nimblegen, Inc., Wilmington, DE (US)

( * ) Notice: Subject to any disclaimer, the term of this patent is extended or adjusted under 35 U.S.C. 154(b) by 799 days.

(21) Appl. No.: 11/101,841

(22) Filed: Apr. 8, 2005

(65) Prior Publication Data

US 2005/0260645 A1 Nov. 24, 2005

Related U.S. Application Data

(60) Provisional application No. 60/560,447, filed on Apr. 8, 2004.

(51) Int. Cl.
*C12Q 1/68* (2006.01)
*C40B 30/00* (2006.01)

(52) U.S. Cl. .............................. 435/6; 506/7; 977/791; 977/795

(58) Field of Classification Search .................. None
See application file for complete search history.

(56) References Cited

U.S. PATENT DOCUMENTS

| 5,143,854 | A | 9/1992 | Pirrung et al. |
| 6,375,903 | B1 | 4/2002 | Cerrina et al. |
| 6,376,191 | B1 * | 4/2002 | Yu et al. ..................... 435/6 |
| 7,144,699 | B2 * | 12/2006 | Chee ........................... 435/6 |

OTHER PUBLICATIONS

Hacia, J.G., "Resequencing and mutational analysis using oligonucleotide microarrays," Nature Genetics Supplement 21:42-47 (1999).
Saiki, R.K., et al., "Genetic analysis of amplified DNA with immobilized sequence-specific oligonucleotide probes," Proc. Natl. Acad. Sci. USA 86:6230-6234 (1989).
Albert, T., et al., "High-throughput prokaryotic and viral mapping and resequencing using custom . . . ," Abstract, Society for General Microbiology 154th Meeting Apr. 2, 2004.
Stjepandic, D., et al., "The genome structure of *Pseudomonas putida*: high-resolution mapping and microarray analysis," Environmental Microbiology 4:819-823 (2002).
Tsolaki, A.G., et al., "Functional and evolutionary genomics of Mycobacterium tuberculosis: Insights from genomic deletions in 100 strains," PNAS 14:4865-4870 (2004).
Wolfgang, M.C., et al., "Conservation of genome content and virulence determinants among clinical and environmental isolates . . . ," PNAS 14:8484-8489 (2003).
Wong, C.W., et al., "Tracking the Evolution of the SARS Coronavirus using High-Throughput, High-Density Resequencing . . . ," Genome Research 14:398-405 (2004).
Yamada, K., et al., "Empirical Analysis of Transcriptional Activity in the *Arabidopsis* Genome," Science 302:842-846 (2003).

* cited by examiner

*Primary Examiner*—Marjorie Moran
*Assistant Examiner*—Jason M Sims
(74) *Attorney, Agent, or Firm*—Quarles & Brady LLP

(57) ABSTRACT

The present invention is an improved method of resequencing DNA using microarrays to rapidly map and identify SNPs, deletions and amplification events present in the genome of an organism. The method is performed by hybridizing a reference and a test genome to two separate arrays with each array exhibiting a specific intensity pattern. The intensity differences between the reference and the test genome arrays are used to produce a mutation map. The mapped differences are resequenced on a set of resequencing arrays to identify specific genetic mutations.

10 Claims, 1 Drawing Sheet

COMPARATIVE GENOMIC RESEQUENCING

CROSS-REFERENCE TO RELATED APPLICATIONS

This application claims priority from U.S. Provisional Patent Application 60/560,447 filed Apr. 8, 2004.

STATEMENT REGARDING FEDERALLY SPONSORED RESEARCH OR DEVELOPMENT

Not applicable.

BACKGROUND OF THE INVENTION

The advent of DNA microarray technology makes it possible to build an array of hundreds of thousands of DNA sequences in a very small area, such as the size of a microscope slide. See, e.g., U.S. Pat. No. 6,375,903 and U.S. Pat. No. 5,143,854, each of which is hereby incorporated by reference in its entirety. The disclosure of U.S. Pat. No. 6,375,903, also incorporated by reference in its entirety, enables the construction of so-called maskless array synthesizer (MAS) instruments in which light is used to direct synthesis of the DNA sequences, the light direction being performed using a digital micromirror device (DMD). Using an MAS instrument, the selection of DNA sequences to be constructed in the microarray is under software control so that individually customized arrays can be built to order. In general, MAS based DNA microarray synthesis technology allows for the parallel synthesis of over 800,000 unique features each containing unique pre-selected oligonucleotides, in a very small area of on a standard microscope slide. The microarrays are generally synthesized by using light to direct which oligonucleotides are synthesized at specific locations on an array, these locations being called features.

With the availability of the entire genomes of hundreds of organisms, for which a reference sequence has generally been deposited into a public data base, microarrays have been used to perform sequence analysis on DNA isolated from such organisms. One technique that can be used to identify a genetic variant is to sequence the genomic DNA of an individual and then to compare that sequence to the reference sequence of that organism. It has been found that many differences in DNA sequence are presented as single variations in DNA sequence, often referred to as single nucleotide polymorphisms or SNPs. The sequence comparison between the test genome and the reference genome of a species has been generally by the brute force mechanism of capillary sequencing to identify the SNPs for that individual.

Specifically, another method of identifying genetic variations has been by resequencing (See Sakai et al., (1989) *PNAS* 86:6230-6234). One method of resequencing that has shown significant results utilizes oligonucleotide microarray technology (Hacia, et al., (1999) *Nature Genetics*, 21(1 Suppl): 42-7.) In particular, this type of resequencing chip consists of a complete tiling of the reference sequence—that is, a chip containing one probe corresponding exactly to each 29-mer in the reference sequence—plus, for each base in this sequence, three mismatch probes: one representing each possible SNP at this position. In theory, any time a SNP is present, the mismatch probe representing this SNP will have a higher intensity signal than the corresponding probe that matches the reference sequence. However, due to unpredictability in signal strength, varying hybridization efficiency, and various other sources of noise, this method typically results in many base positions whose identities are incorrectly predicted. As such, alternative methods for efficiently and accurately resequencing DNA using microarrays to identify mutations in the genomes of organisms would be a desirable contribution to the art.

BRIEF SUMMARY OF THE INVENTION

The present invention is summarized as an improved method of high-throughput mutation mapping and resequencing of genomes using Maskless Array Synthesis (MAS) technology. In practicing the invention, mutation mapping is performed using a comparative genomic hybridization approach to rapidly map virtually all SNP, deletions and amplification events present between a sequenced reference genome and a test genome. In general, the method is performed by hybridizing a reference genome to a first hybridization array set, generating a reference intensity pattern. Likewise, a test genome is then hybridized to a second hybridization array set, generating a test intensity pattern. The difference between the test and the reference intensity patterns is then mapped, thus generating a mutation map for the test genome. The mapped mutations are then resequenced to identify the genetic mutations in the test genome.

One aspect of this invention is that it provides a method for resequencing the entire genome of the live oral typhoid vaccine, *Salmonella enterica* Ty21a, mapping greater than 500 novel mutations in the 4.8 Mbase genome and identifying the mapped mutations.

Other objects advantages and features of the present invention will become apparent from the following specification.

DETAILED DESCRIPTION OF THE INVENTION

Figure 1:
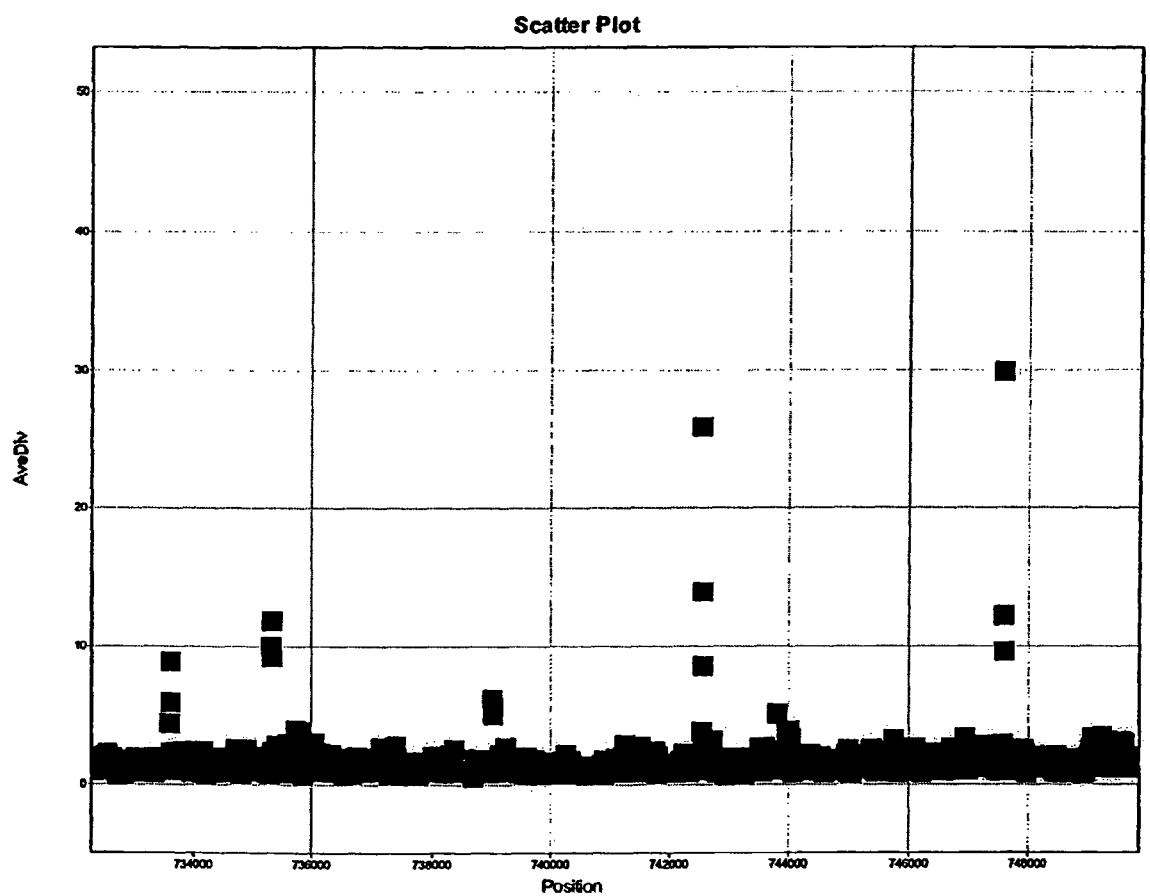
FIG. 1 is a graph of probe intensity ratios plotted against genome position.

The present invention broadly provides an improved method of resequencing DNA using microarrays. Specifically, the invention provides a method for high-throughput mutation mapping and resequencing genomes for preferably several members of the same species facilitated by Maskless Array Synthesis (MAS) technology. In practicing the invention, mutation mapping is performed using a comparative genomic hybridization approach to rapidly and accurately map and identify virtually all SNP, deletions and amplification events present between a sequenced reference genome and a test genome. In general, the method is performed by hybridizing a reference genome to a first microarray having a set of features intended to hybridization the reference genome to generate a reference intensity pattern. Likewise, a test genome is then hybridized to a second microarray having a similar set of features to generate a test intensity pattern. The difference between the test and the reference intensity patterns is then mapped, thus generating a mutation map for the test genome. The mapped mutations are then resequenced using additional microarrays constructed to identify with specificity the genetic mutations in the test genome.

So, again, the benefit of this method of genomic re-sequencing is the dramatically reduced number of microarrays necessary to test for every possible sequence difference in a whole genome. Remember that in the previous ways to perform re-sequencing four different features are required for each nucleotide in the genome. Even using microarrays with many features, this requires many microarrays. For this new method, the first round of reference and test genomic hybridizations are done with against genomic tiling arrays that can test over more than one nucleotide. For example, in the examples below the first set of microarrays were tiled staggered by seven nucleotides. Then, after the reference genome is hybridized against that first microarray or microarray set. Then the same microarray or microarray set is hybridized with the test genome. The data from the two hybridization protocols is then examined to located any differences in discovered intensity difference, indicating a possible difference in nucleotide sequence between the test genome and the reference genome. Then a new set of microarrays is designed to just re-sequence with all four mis-matches only those nucleotides spanned by the probes which were identified in the first round of hybridizations. These are, of course, then tested against only the test genome to precisely identify the nucleotide variants in the test genome. In our hands, we have been able to perform definitive re-sequencing of microbial genomes using this method using only a fraction of the number of arrays that would be needed to just do brute force total re-sequencing of all the nucleotides of the genome in a single process.

General Materials and Methods

In accordance with the present invention "Array-Based Resequencing" (ABR) was used to sequence genes based on the differential hybridization of genomic fragments to short perfect-match (PM) and mismatch (MM) oligonucleotides in different features in a microarray. On the array platform of the invention, each nucleotide to be queried in the genome was matched by a complementary nucleotide located at the $15^{th}$ position of a PM 29-mer oligonucleotide ("oligo") in a feature on the array. For each PM oligo, features including probes representing the 3 possible mismatch nucleotides at the $15^{th}$ position were also synthesized on the array. Probes suitable for synthesis on the array can be of any reasonable length, such as for example, up to and greater than 100 base pairs. Also, the mismatch is not required to be at the central base position of each probe, but it can vary within the probe sequence. The differences in hybridization signal intensities between sequences that bind strongly to the PM oligo and those that bind poorly to the corresponding MM oligos make it possible to discern the correct base at a given sequence position.

For example, each array of the invention, constructed using the MAS instrument, contains 380,000 features each containing unique probes, each probe being a 29-mer with 4 probes per base position for each strand. Probes for both forward and reverse strands were included on the array, allowing 47,500 bases to be resequenced per array. A total of 101 resequencing array designs were synthesized based on the entire 4.8-Mb *S. enterica* serovar Ty2 genome.

The genomic DNA from *S. enterica* serovar Ty21a was amplified, digested and labeled as described below. For example, 1 µg of *S. enterica* serovar Ty21a was amplified in 10 reactions using the Repli-g whole genome amplification kit (Molecular Staging, *New Haven, Conn.*), resulting in ~500 µg of amplified DNA. For each array hybridization, 5 µg of amplified genomic DNA was digested with 0.1 U DNase I (Amersham Biosciences, Piscataway, N.J.) and 1×One-Phor-All buffer (Amersham) in a total volume of 20 µL. DNase I was inactivated by incubation at 97° C. for 15 minutes. Sample was end-labeled with 1 µL Biotin-N6 ddATP (Perkin Elmer, Wellesley, Mass.) and 25 U Terminal Deoxynucleotidyl Transferase (Promega, Madison, Wis.) at 37° C. for 90 minutes, and terminal transferase was inactivated by incubation at 97° C. for 15 minutes.

Before application of the labeled sample to the array, the resequencing arrays were pre-hybridized with 1×NimbleGen Resequencing Buffer (NimbleGen Systems, Madison, Wis.). Samples were heated to 95° C. for 5 minutes, heated to 45° C. and centrifuged for 5 minutes at >12000 g. Each labeled DNA sample was then applied to the arrays, which were placed in a customized hybridization chamber and incubated at 45° C. for 14 to 16 hours in a rotisserie oven. The arrays were then washed with nonstringent wash buffer (6×SSPE, 0.01% [v/v] Tween-20), followed by two 5 minute washes in stringent wash buffer (100 mM MES, 0.1 M NaCl, 0.01% [v/v] Tween-20) at 47° C. The arrays were stained with a solution containing Cy3-Streptavidin conjugate (Amersham Biosciences, Piscataway, N.J.) for 10 minutes, and washed again with nonstringent wash buffer. The Cy3 signal was amplified by secondary labeling of the DNA with biotinylated goat anti-streptavidin (Vector Laboratories, Burlingame, Calif.). The secondary antibody was washed off with non-stringent wash buffer, and the array was re-stained with the Cy3-Streptavidin solution. Finally, the stain solution was removed, and array was washed in non-stringent wash buffer followed by a 30 seconds wash in 0.5×SSC and 15 seconds wash in 70% ethanol. Arrays were spun dry in a custom centrifuge and stored prior to being scanned.

Microarrays were then scanned at 5 µm resolution using the Genepix® 4000b scanner (Axon Instruments, Inc., Union City, Calif.). The image was interpolated and scaled up 2.5× in size using NIH Image software (rsb.info.nih.gov/nih-image/), and pixel intensities were extracted using NimbleScan™ Software (NimbleGen Systems, Inc. Madison, Wis.). Sequence calls were made based on statistical analysis of the hybridization intensities combining data from both strands using a preferred, novel Machine-Learning algorithm that utilizes a classification technique called K-nearest-neighbors, a well-known classification algorithm within the Machine Learning community. It is called a classification algorithm because it is used to classify examples based on known features. This particular algorithm consists of plotting each example in feature space and then, for each of these examples, finding the K nearest to it in this feature space. The categories of these K neighbors dictate the prediction. If greater than some threshold P of these neighbors is a positive example, the prediction is positive. Otherwise, the prediction is negative. The number of positive examples among the K neighbors can further be used as a measure of confidence in the prediction. It is noted that the appropriate value for k and useful definitions of nearness and feature space tend to vary between learning tasks. (See commonly owned U.S. Provisional Application No. 60/539,220 filed Jan. 26, 2004, now U.S. patent application Ser. No. 11/043,294 filed Jan. 25, 2005. This application is incorporated by reference herein in its entirety.) Other similar algorithms for identifying positives can also be used, or the data can be manually evaluated to derive the same information.

One advantage of this method of analyzing microarray hybridization data is its ability to accurately differentiate potential SNPs from chip noise and variations in hybridization conditions. Also, unlike other methods of microarray data analysis, this method does not require a high-resolution scanner and furthermore does not require any tuning outside of the single chip being analyzed. This preferred method uses only the mean signal intensity of each probe on the chip (the array) and no data from outside of the chip.

Similarly, the comparative genomic hybridization array designs were synthesized as described above. Genomic DNA from the *S. enterica* Ty2 (reference) and Ty21a (test) were amplified, digested and labeled as above. Each sample was then hybridized to two separate 4-array sets. It is noted that the number of array sets in any particular experiment can vary depending on the size of the genome being analyzed. The arrays were scanned and images were extracted as described above. The difference in intensity patterns between the reference and the test genome was mapped, thus generating a mutation map for the test genome. The mapped mutations were then resequenced on new custom arrays particularly designed to identify the genetic mutations in the test genome. This method provides a rapid and cost effective method for mapping and identifying mutations in the entire genomes of microbial and viral strains. This ability to efficiently define microbial and viral genomes is becoming increasing important for identification of novel drug and vaccine targets.

The following examples are provided as further non-limiting illustrations of particular embodiments of the invention.

EXAMPLES

Although the invention includes many embodiments, in one embodiment the method of the invention was used to map and identify SNPs found in the genome of live attenuated typhoid vaccine, *Salmonella enterica* serovar Typhi Ty21a. By way of background *Salmonella typhi* is the causative agent of typhoid fever. It is estimated that there are 16 million cases of typhoid each year world-wide, resulting in 500,000 deaths. Recent reports have indicated the emergence of multi-drug resistant forms of *S. enterica* serovar Typhi, making infections increasingly difficult to treat. This necessitates the identification of novel drug and vaccine targets. The live oral typhoid vaccine Ty21a was produced by randomly mutagenizing the infectious *S. enterica* Ty2 strain with nitrosoguanidine. Ty21a is known to have a number of characteristics thought to be involved in attenuation, including galE and rpoS mutations, the lack of Vi polysaccharide, and weak acid tolerance. Despite these characteristics, the exact nature of its attenuation has never been determined. Because of this, the utility of random mutagenesis methods to develop live vaccines has been questioned. Accordingly, it is envisioned that development of novel technologies, such as those described by the present invention for rapidly and cost effectively defining microbial and viral genomes may lead to identification of novel drug and vaccine targets. This can aid in validating the utility of random mutagenesis and evolution based techniques in vaccine development.

In order to map and identify SNPs in the *S. enterica* serovar Typhi Ty21a genome, maskless array technology was used to rapidly design and produce high-density oligonucleotide microarrays directly from a digital database of primer sequences. It is noted that each array design was capable of covering a genome length of ~1.3 Mbases. As described above, the technology utilizes photo-deposition chemistry in conjunction with Digital Light Processing to perform in situ DNA synthesis directly in the array. Arrays of >380,000 oligonucleotides were synthesized in approximately three hours. Maskless array technology was used to design and synthesize a 4-array set that tiled the sequenced *S. enterica* Ty2 reference genome with a 29-mer probe every 7 bases for both strand. Two 4-array sets were hybridized separately to whole genome amplified, fragmented, and labeled genomic DNA from the Ty2 reference genome, and the Ty21a test genome. The ratio of probe intensities were calculated and plotted against genome position, as shown in FIG. 1. This plot shows data from a small portion of the *S. enterica* genome colorimetrically illustrating probes with similar hybridization characteristics, identical target sequences in both genomes and probes with significantly higher intensity in the reference genome than the test genome. The difference in probe intensity patterns between the reference and test genomes was mapped, thus generating a map of sequence mutations (e.g., SNPs) within the test genome. The map of mutations was resequenced using a set of custom resequencing arrays to identify the location and sequence of specific genetic mutations.

Specifically, once the genetic differences between the reference and test genomes were mapped, a custom algorithm was used to select probes with ratios significantly different from the background as described herein. Custom software was then used to automatically generate resequencing arrays to specifically resequence all genome positions spanned by probes with significantly shifted ratios. A total of 95,726 positions in the genome were selected for resequencing, which spanned two resequencing arrays. The resequencing arrays were hybridized with DNA from the Ty21a strain, identifying 497 SNPs. Thirty one of these SNPs were randomly selected, amplified and validated using capillary sequencing. All but one SNP validated, and the single non-validating SNP had a clear double peak present in the sequence chromatogram, indicating the presence of a mixed population, with the resequencing array calling one species and capillary sequencing calling the other (data not shown).

The entire 4,791,958 bp *S. enterica* Ty21a genome was then resequenced using traditional array-based resequencing (ABR) using 101 different array designs to span the entire genome. The data obtained from the CGR strategy was then compared with the ABR data. Applicants found that the CGR approach resulted in a significantly lower estimated false positive rate, (0.0004% for CGR vs. 0.003% for ABR), identified >97% of the SNPs identified by ABR, and required less than 10% of microarrays (10 for CGR vs. 101 for resequencing.)

To confirm the above results, the genomic DNA from the Ty21a strain was treated as described above and hybridized to each array design. At least 98,180 bp (2.05% of the genome) were removed from analysis due to probe sequence redundancies in the genome. The remaining 98.7% of the genome was called with high confidence, resulting in an over-all call rate of 96.7%, identifying 623 SNPs. Of these SNPs, 488 were identified by CGR. Only 8 of 36 SNPs randomly selected SNPs identified by ABR but not by CGR validated using capillary sequencing. Using these validation results, the number of true SNPs identified by resequencing, but missed by CGR was estimated to be 32, while the number of false positives identified by resequencing is estimated to be 114, suggesting a resequencing accuracy of 99.997% (121 false positives in ~4.8 million calls). Based on the above results, there were 20 positions that were identified by CGR but not by resequencing. These positions did not validate by capillary sequencing, suggesting a CGR accuracy of 99.9995% (23 false positives in ~4.8 million calls).

The false negative rate for resequencing should be the same as the overall call rate, assuming SNPs are distributed equally between called and non-called portions of the genome. Validation of the SNPs called by resequencing was estimated to be the true number at 509. Since 98.7% of the unique portion of the genome was called by resequencing, it is estimated that 7 uncalled SNPs in the unique portion of the genome, resulted in a false negative rate of 0.00015%. CGR identified 477 of the 509 estimated to be true SNPs, and failed to identify 32 SNPs, resulting in a false negative rate of 0.00066%.

The overall false positive rate for CGR was estimated to be almost 20 fold lower than ABR, based on SNPs validation by capillary sequencing, even though ABR requires more than ten times as many microarrays. The majority of false positives produced by ABR appear to be the result of non-specific hybridization to mismatch resequencing probes. This is an infrequent event happening on average once every ~40,000 bases. On a genome scale, however, this can result in a significant number of false positive base calls. CGR, however, is less likely to produce similar false positive results, because the arrays used in the initial mapping phase do not contain mismatch probes. Only probes that display an intensity difference between the reference and test genome are chosen for resequencing. Since the resequencing technique used in the second phase of CGR is identical to ABR performed on select positions across the genome, the number of false positives per base call should also be similar. Therefore, the number of false positives is predicted to be approximately 2 in 95,726 base calls.

Applicants note that the majority of these probes proved to be false positives by the resequencing arrays used in the second phase of CGR, and thus had little impact on the final data set. CGR reports more may be related to the fact that the Ty21a strain was originally produced by random mutagenesis using nitrosoguanidine (NG). NG is known to produce primarily C→T or G→A transitions. Of the 500 SNPs identified by CGR, >94% are C→T or G→A transitions. These transitions occasionally introduce internal stop codons into open reading frames. Of the SNPs identified in the Ty21a genome, 33 produce internal stop codons in annotated genes, potentially producing gene "knock outs". Two of the genes found to contain an introduced internal stop codons are the tviE and rpoS genes, producing products that lack the C-terminal 11 and 43 amino acids respectively. The Ty21A strain is know to lack a Vi polysaccharide capsule. The product of the tviE gene is thought to play a role in Vi polysaccharide biosynthesis. The RNA polymerase RpoS is mutated in both the Ty2 and Ty21a strains. This mutation has been hypothesized to be involved in stress response, reducing fitness, and consequently virulence. It is possible that other mutant RNA polymerases, such as RpoC, could also be involved in reduced virulence. Furthermore, it is envisioned that genetic and biochemical studies of these and other mutated genes discovered as a result of the methods described by the invention will lead to a better understanding of the virulence of *Salmonella Typhi*, and will result in the identification of novel drug and vaccine targets.

In addition to the identification of SNPs, the methods of the invention have also been used to produce a fine-map of deletion and amplification events. For example, the invention was used to resequence the genomes of 16 clinical isolates of the SARS coronavirus with >99.99% accuracy. Also, the invention was used to resequence and effectively map large deletions in, for example, the *E. coli* 0157:H7 genome relative to the *E. coli* K12 genome. By comparing their two genome maps, applicants were able to identify a duplication of approximately 100,000 bp present in an *E. coli* K12 strain that was engineered for growth on glucose.

Furthermore, applicants envision that the comparative genomic resequencing strategy of the invention may be generally used for identifying mutations in haploid species or a haploid preparation of a diploid genome. The invention may also be helpful for large resequencing projects that use BACs (bacterial artificial chromosomes, having an average size of 100 kb), plasmids, phosmids, YACs (yeast artificial chromosomes) or any other library or preparation that results in the isolation of haploid sections of a genome. Specifically, with respect to haploid organisms, applicants have found the invention produces results similar to the published results in SNP identification rate as compared to the best known of the current statistical methods. It is also anticipated that there will be regions within the genomes of interest that are particularly difficult regions with highly variable patterns and will require the use of conventional sequencing methods.

It is understood that certain adaptations of the invention described in this disclosure are a matter of routine optimization for those skilled in the art, and can be implemented without departing from the spirit of the invention, or the scope of the appended claims.

We claim:

1. A method for identifying genetic mutations in a test genome of an organism relative to a reference genome of the an organism, the method comprising the steps of:
   a) hybridizing the reference genome and the test genome in separate hybridization reactions to a genomic tiling array that comprises a plurality of probes that tile the reference genome across a plurality of regions having a stagger of more than one nucleotide to produce a reference intensity pattern and a test intensity pattern;
   b) identifying in the plurality of regions a subset of regions of possible genetic mutation in the test genome in which the test intensity pattern differs from the reference intensity pattern; and
   c) resequencing the subset of regions of possible genetic mutation in the test genome on a resequencing array.

2. The method of claim 1 wherein the test genome is haploid.

3. The method of claim 1 wherein the test genome is a *Salmonella enterica* ty21a genome.

4. The method of claim 1 wherein the test genome is a haploid preparation of a diploid genome.

5. The method of claim 1 wherein the regions that span more than one nucleotide tile the reference genome with a stagger of seven nucleotides.

6. The method of claim 1 wherein the resequencing array includes a probe for each possible nucleotide at each nucleotide position in each region in the subset.

7. The method of claim 1 wherein the genetic mutation is a single nucleotide polymorphism.

8. The method of claim 1 wherein the genetic mutation is an insertion.

9. The method of claim 1 wherein the genetic mutation is a deletion.

10. The method of claim 1 wherein the genetic mutation is an inversion.

* * * * *